(12) United States Patent
Chin et al.

(10) Patent No.: US 6,348,037 B1
(45) Date of Patent: *Feb. 19, 2002

(54) DEVICE AND METHOD FOR REMOTE VESSEL LIGATION

(75) Inventors: Albert K. Chin; Edwin J. Heavka, both of Palo Alto; John P. Lunsford, San Carlos; Jeffrey W. Baxter, San Jose, all of CA (US)

(73) Assignee: Origin Medsystems, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/521,279

(22) Filed: Mar. 7, 2000

Related U.S. Application Data

(63) Continuation of application No. 09/200,218, filed on Nov. 25, 1998, now Pat. No. 6,162,173, which is a continuation-in-part of application No. 09/102,723, filed on Jun. 22, 1998, now Pat. No. 5,895,353.

(51) Int. Cl.[7] .............................................. A61B 17/02
(52) U.S. Cl. ...................................... 600/235; 600/209
(58) Field of Search ................................ 600/209, 210, 600/201, 235

(56) References Cited

U.S. PATENT DOCUMENTS

| | | | | |
|---|---|---|---|---|
| 4,651,733 A | * | 3/1987 | Mobin-Uddin | 600/235 |
| 5,284,128 A | * | 2/1994 | Hart | 600/209 |
| 5,512,037 A | * | 4/1996 | Russell et al. | 600/201 |
| 5,722,934 A | * | 3/1998 | Knight | 600/210 |
| 5,895,352 A | * | 4/1999 | Kleiner | 600/209 |
| 6,162,173 A | * | 12/2000 | Chin et al. | 600/235 |

* cited by examiner

Primary Examiner—Paul J. Hirsch
(74) Attorney, Agent, or Firm—Fenwick & West, LLP

(57) ABSTRACT

A retractor and a surgical tool are positioned within a cannula, and a dissection cradle of the retractor is positioned at the distal end of the cannula. The retractor includes a first portion with an axis approximately parallel to the axis of the cannula and a second portion with an axis skewed relative to the axis of the cannula. The dissection cradle is located at the distal end of the second portion of the retractor, and may include two substantially parallel, spaced legs with the retractor shaped in a loop between and in a plane skewed relative to the axes of the legs, and with the loop directed away from the surgical tool. Thus, in operation, when the surgeon locates a vessel and side branch of interest, the surgeon extends the retractor to cradle the vessel in the dissection cradle. Once cradled, the retractor may be fully extended to urge the vessel away from the axis of the cannula to isolate the side branch for exposure to the surgical tool. The dissection cradle may include a forward shoulder for positioning a suture loop. A forwardly-projecting tensioner supports a length of suture from the loop to maintain the loop in tension for transport along the vein. During advancement, the suture loop is safely maintained in place due to the tension provided by the tension mount and the support provided by the shoulder. Upon reaching the surgical site of interest, the retractor is retracted, causing the suture loop to be displaced onto the vein at the desired position. In one embodiment, the loop is tightened by pulling on the length of suture near the proximal end of the cannula to constrict the suture loop about the vein near the distal end of the cannula.

3 Claims, 13 Drawing Sheets

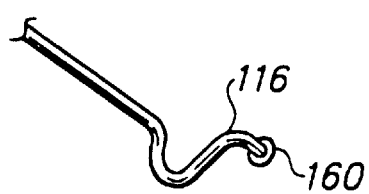
FIG. 9F
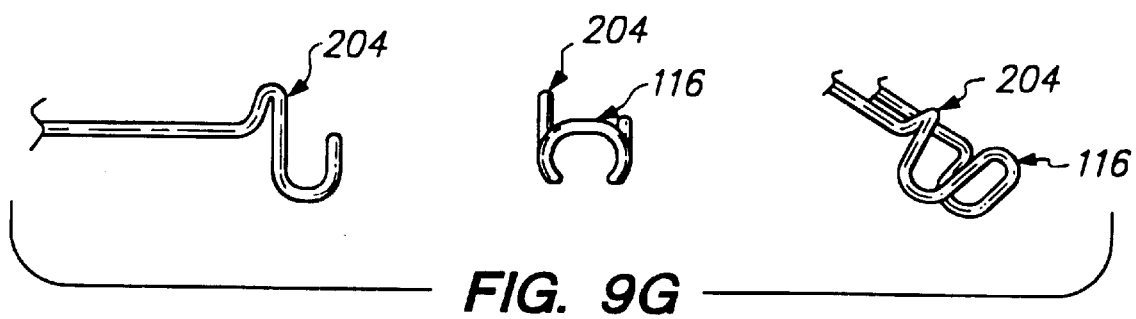
FIG. 9G
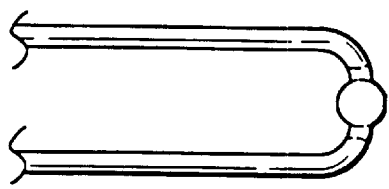 
FIG. 10A  FIG. 10B
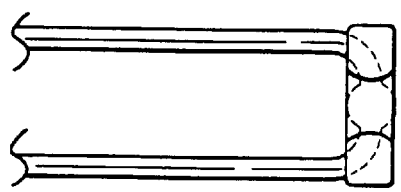 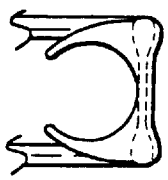
FIG. 10C  FIG. 10D

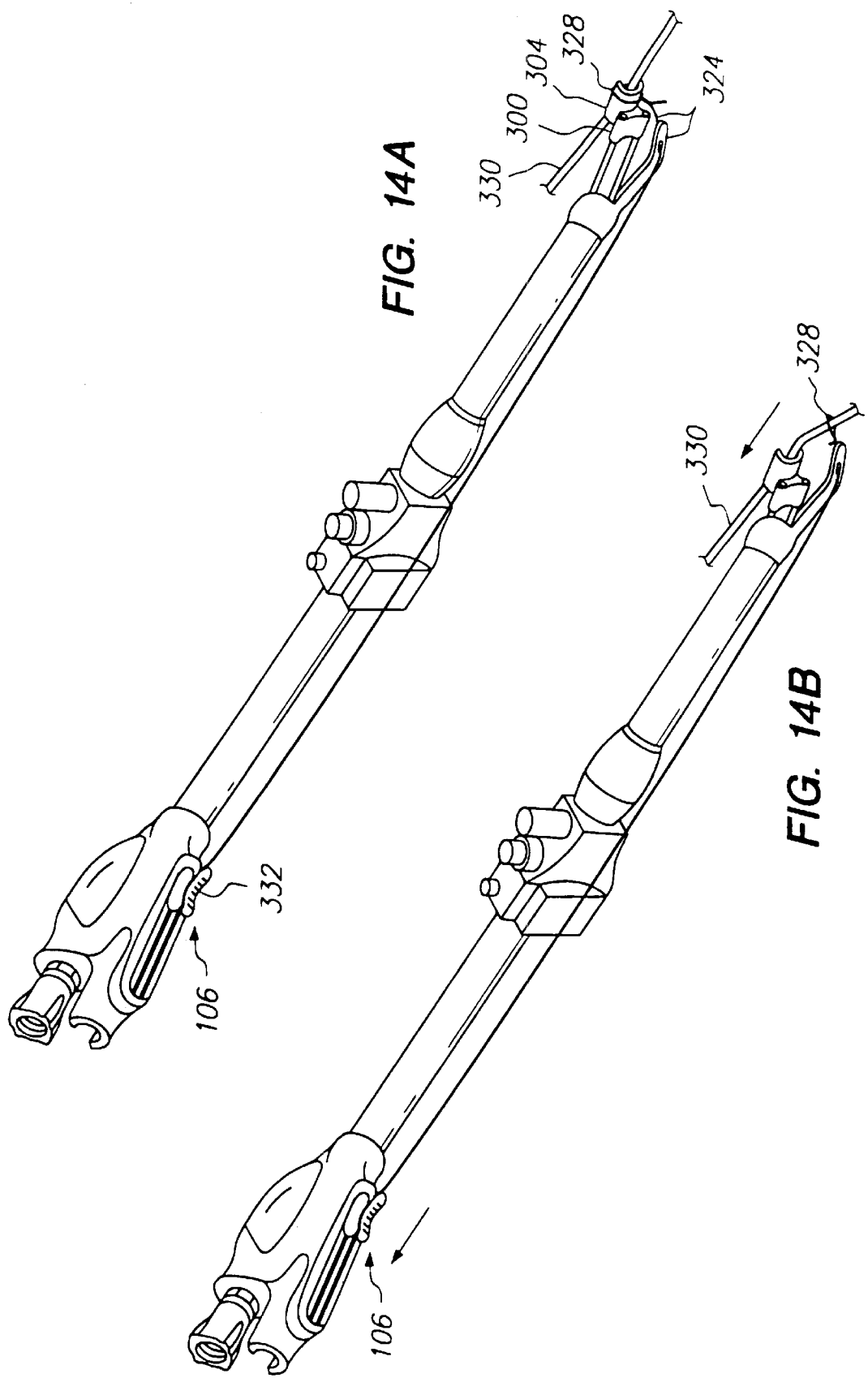

DEVICE AND METHOD FOR REMOTE VESSEL LIGATION

CROSS-REFERENCE TO RELATED APPLICATIONS(S)

The present application now U.S. Pat. No. 5,895,353 is a continuation of application Ser. No. 09/200,218 filed on Nov. 25, 1998, now U.S. Pat. No. 6,162,173, which is incorporated herein in its entirety, and a continuation-in-part application of application Ser. No. 09/102,723 filed on Jun. 22, 1998.

FIELD OF THE INVENTION

This invention relates to a cannula used for vessel retraction, and more particularly to a cannula and method that includes an endoscopic retractor for vessel ligation.

BACKGROUND OF THE INVENTION

Certain cannulas have surgical tools located within the cannula for performing surgical operations on a vessel of interest. The cannula is inserted into a surgical site with the distal end of the cannula positioned near the vessel of interest. An endoscope positioned within the cannula allows the surgeon to view the target area, and allows the surgeon to position the surgical tool correctly. One common procedure is to ligate a vessel or other tissue by tightening a suture loop tied as a slipknot on the vessel before transection to provide hemostasis to the vessel.

However, surgeons encounter several difficulties in ligation procedures. In one ligation procedure, a second incision must be made at the opposite end of the vessel of interest to ligate and transect the vessel. Multiple incisions are invasive and should be minimized if possible. In order to avoid this second incision, some conventional methods require tying a suture loop around the vessel, and pushing the loop along the vessel with a knot pusher until the opposite end is reached. Then, the loop is tightened to provide ligation. However, this procedure is difficult because the slipknot often catches on stumps of cut tributaries or other tissue, and then constricts around the vessel at the wrong position. Also, there is no easy method for transecting the vessel after the suture loop is tied to the vessel without potentially prematurely severing the suture.

Thus, a device and method is needed to allow remote, one-incision, ligation of a vessel which allows a suture loop to be moved reliably to the site of interest, and ensures that the transection instrument is able to transect the vessel, and cut the suture.

SUMMARY OF THE INVENTION

In accordance with the present invention, a retractor is positioned within a cannula with a dissection cradle end of the retractor positioned at the distal end of the cannula. The retractor includes a first portion that has an axis approximately parallel to a central axis of the cannula, and a second portion that has an axis which is at an angle with respect to the central axis of the cannula. The dissection cradle is located at the distal end of the second portion of the retractor. In another embodiment, the retractor includes two legs having substantially parallel axes that selectively protrude from the distal end of the cannula. The protruding legs support the dissection cradle formed in the shape or a loop that is positioned in a plane skewed relative to the axes of the legs, with a bottom of the loop directed away from the cannula. Thus, in operation, when the surgeon locates a vein and side branch of interest, the surgeon extends the retractor to cradle the vein in the dissection cradle. Once cradled, the retractor may be fully extended, pulling the vein away from the axis of the cannula causing the side branch to be isolated and exposed to a surgical tool. The surgical tool may then be extended from within the cannula to operate on the isolated and exposed side branch.

In another embodiment, the top of the loop of the dissection cradle is flat and thin, allowing atraumatic support of the vein, and minimizing contact between the retractor and the surgical tool. In yet a further embodiment, the retractor includes a single leg with the loop formed by the one leg of the retractor, and with a stopper coupled to the distal end of the retractor. In still another embodiment, the cannula comprises a sliding tube which encases the retractor, and in a first position is extended out to encase the second portion of the retractor, and in a second position is extended to encase only the first portion of the retractor. In response to being in the first position, the second and first portions of the retractor are both approximately parallel to the axis of the cannula. In the second position, the second portion of the retractor is skewed relative to the axis of the cannula.

In accordance with an alternate embodiment of the present invention, a retractor is positioned within a cannula with a dissection cradle end of the retractor positioned at the distal end of the cannula. The dissection cradle comprises a shoulder part and a curved channel part. Suture forming a suture loop is threaded through a hole in a tension mount that is fixed to the distal end of the cannula and is abutted against the distal end of the shoulder. Upon advancement to the surgical site of interest, the suture loop is safely maintained in place due to the tension provided by the tension mount and the support provided by the shoulder. The curved channel provides a groove in which the vessel of interest may be cradled. Upon retraction of the retractor, the suture loop is displaced onto the vessel at the desired position for ligation. In one embodiment, the loop is tightened by detaching the proximal end of the suture from the cannula and pulling on the suture, constricting the suture loop. In an alternate embodiment, a manual controller for retracting the retractor is attached to the proximal end of the suture. Upon slidable retraction of the manual controller, the retractor is retracted, the loop is displaced onto the vessel, and the loop is tightened.

In a further embodiment, a transecting device is positioned within the cannula. The distal end of the tension mount is positioned to allow the distal end to be proximal to the shoulder of the dissection cradle responsive to the shoulder being in an axial position relative to the tension mount. This results in the suture and vessel being reliably positioned within reach of the transecting device for transection of the vessel and cutting of the suture.

Finally, in a preferred embodiment, the retractor has a distal end having an axis skewed relative to the central axis of the cannula, thus facilitating accurate positioning of the vessel and suture for transection and cutting and ensuring the proper displacement of the suture loop onto the vessel in response to the retraction of the retractor.

BRIEF DESCRIPTION OF THE DRAWINGS

FIG. 7b is a side view of the retractor 112 of FIG. 7a.

FIG. 9f illustrates multiple views of a fifth alternate embodiment of cradle 116.

FIG. 9g illustrates multiple views of an embodiment of cradle 116 having a spur.

FIG. 10a illustrates a top view of an embodiment of the cradle 116 of FIG. 9c without a "C" ring.

FIG. 10b illustrates a side view of the cradle 116 of FIG. 10a.

FIG. 10c illustrates a top view of the cradle 116 of FIG. 9c with the "C" ring attached.

FIG. 10d illustrates a side view of the cradle 116 of FIG. 10c.

FIG. 14a illustrates a perspective side view of cannula 100 with retractor 112 extended.

FIG. 14b illustrates a perspective side view of cannula 100 with retractor 112 retracted.

DETAILED DESCRIPTION OF THE PREFERRED EMBODIMENTS

Figure 1:
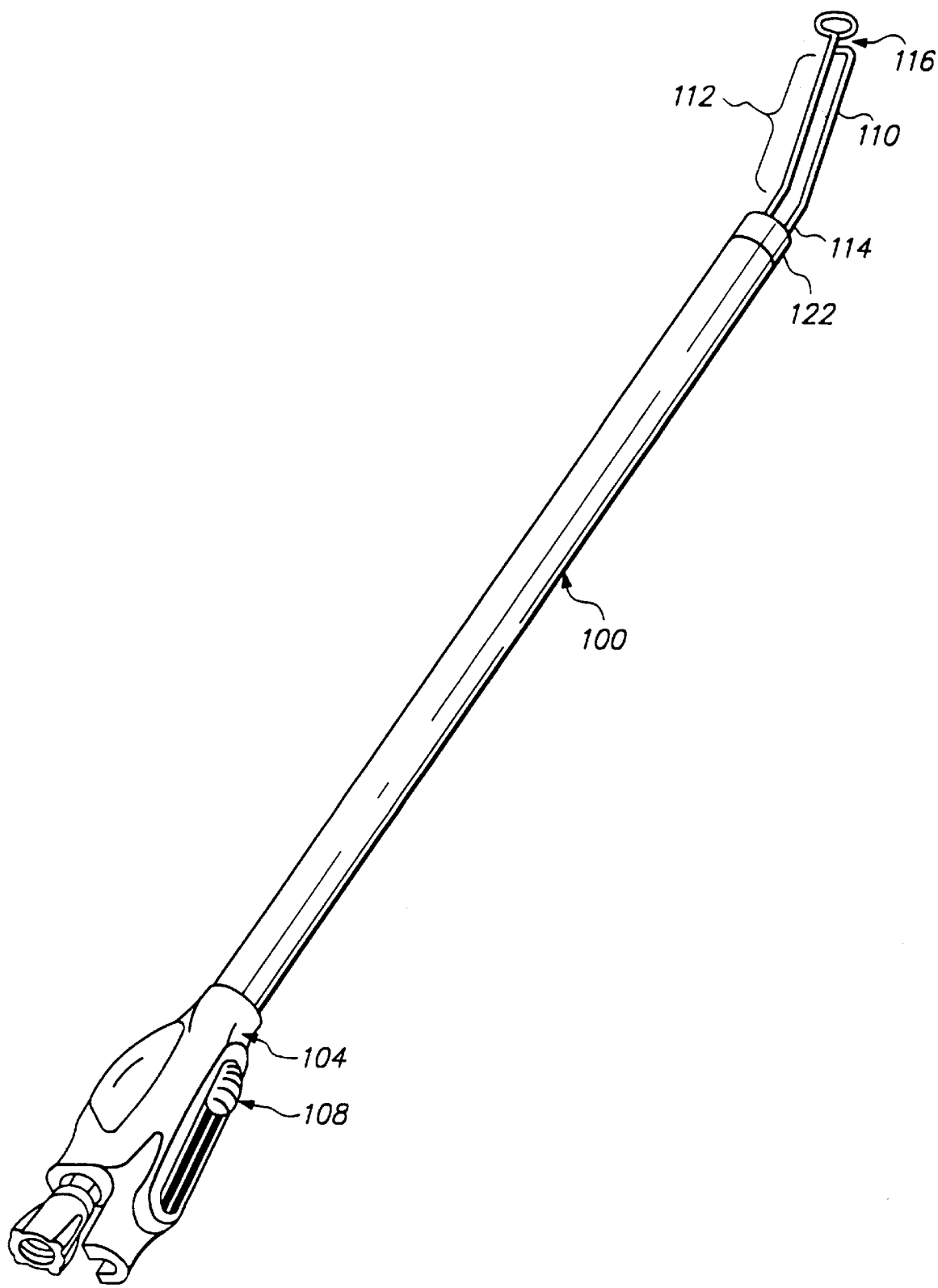
FIG. 1 is a perspective view of a preferred embodiment of cannula 100 showing retractor 112 in an extended position.

FIG. 1 illustrates a perspective view of a preferred embodiment of cannula 100 showing retractor 112 in an extended position. Cannula 100 includes an outer housing 102 of bioinert material such as polymed UD that may be approximately 12" to 18" in length. The proximal end of the cannula 100 is disposed in handle 104 that includes a button 106 which is coupled to retractor 112 for controlling the translational movement of retractor 112, as described in more detail below.

Figure 2A:
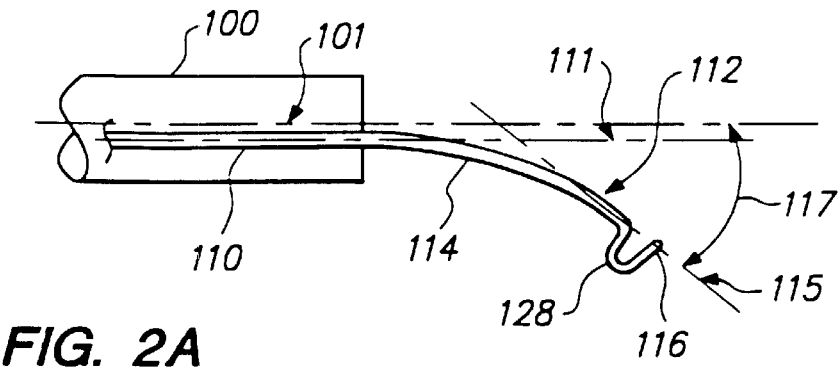
FIG. 2*a* is a cut-away side view of retractor 112 and cannula 100.

The distal end of the cannula houses a retractor 112, and optionally an endoscope 126 and a surgical tool 120, described below. FIG. 2a illustrates the retractor 112 in more detail. In one embodiment, retractor 112 is formed of resilient wire which has a smooth bend intermediate to a first portion 110 and a second portion 114 of the retractor. The retractor 112 is described as having two portions for ease of description, although the retractor 112 may be formed as an integrated structure. However, retractor 112 may also be manufactured from two separate portions 110, 114 that are coupled together. The first portion 110 of the retractor 112 is positioned within the cannula 100 with the axis 111 of the first portion 110 approximately parallel to the axis 101 of the cannula 100. The second portion 114 is positioned to bend away from the central axis 101 of the cannula. The angle 117 of displacement between the axis 115 of the second portion and the central axis 101 of cannula 100 may be any angle from zero to 180 degrees. The second portion 114 includes a dissection cradle 116 at the distal end of the second portion 114. The retractor 112 may be formed of bioinert material such as stainless steel, or a polymer such as nylon or polyetherimide, or other appropriately strong and springy plastic. In one embodiment, the reactor 112 includes a coating for lubrication, insulation, and low visual glare using, for example, parylene or nylon 11.

Figure 2B:
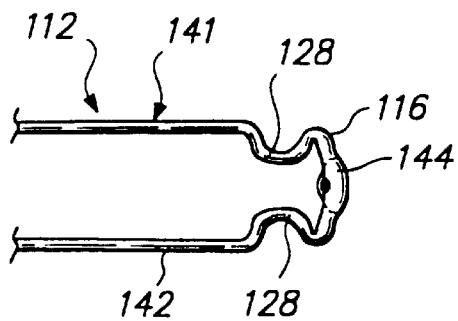
FIG. 2*b* is a top view of retractor 112.

FIG. 2b illustrates the retractor 112 formed with two legs. The legs 141, 142 of the retractor 112 at the distal end form the dissection cradle 116 in a loop or "U" shape, as shown in FIG. 2a. The top portion 144 of the U-shaped bend is preferably flattened to provide additional surface area for atraumatically supporting a vein 118 or vessel of interest. The side arches 128 of the dissection cradle 116 are used for skeletonizing or dissecting the vein from the surrounding tissues, as well as acting as walls to keep the vessel captured within the arch. The several embodiments of dissection cradle 116 are described in more detail below.

Figure 3A:
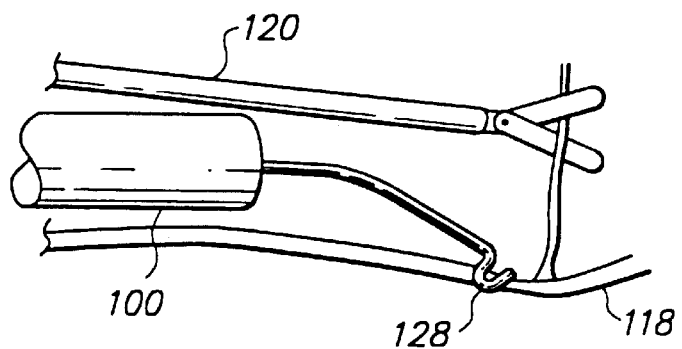
FIG. 3*a* is a perspective side view of cannula 100 with a saphenous vein positioned within the cradle 116.

FIG. 3a illustrates a perspective view of the cannula 100 in accordance with the present invention with the retractor fully extended, holding a saphenous vein 118, and also illustrates an external surgical tool 120 disposed adjacent the cannula 100 for performing a surgical operation, for example, severing a tributary or side branch of the vein 118. The vein is positioned within the side arches 128 of the cradle 116. The dissection cradle 116 may be used to cradle a vein. vessel, tissue or organ of interest, and surgical tool 120 may be any surgical tool suitable for performing a surgical procedure near the dissection cradle 116.

Figure 3B:
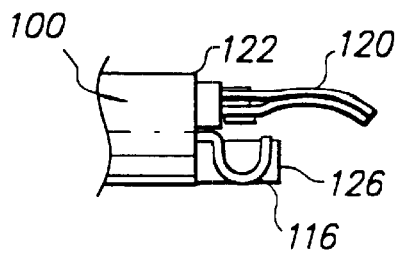
FIG. 3b is a perspective side view of the distal end 122 of cannula 100 in an embodiment in which an endoscope 126 and a surgical tool 120 are present and partially extended.
Figure 3C:
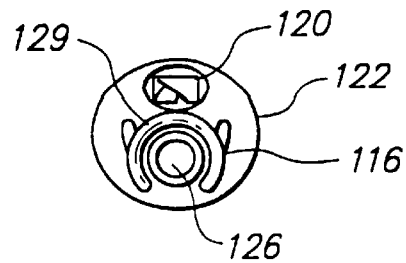
FIG. 3c is a front view of the distal end 122 of cannula 100 in which the surgical tool 120 and the retractor 116 are partially extended, and an endoscope 126 is present.

FIG. 3b illustrates a perspective view of cannula 100 in an embodiment in which the surgical tool 120 is positioned within the cannula 100, and an endoscope 126 is present. In this embodiment, cradle 116 preferably overlays the endoscope 126 with sufficient clearance to facilitate relative movements thereof. However, the endoscope may also be located adjacent the surgical tool 120. In one embodiment, endoscope 126 is positioned with cannula 100 to allow a clear field of view upon extension of the retractor 112. Surgical tool 120 is illustrated as scissors, used to sever a tributary or side branch of a saphenous vein 118. In this embodiment, surgical tool 120 is maximally displaced from the cradle 116 at the cannula end 122. More specifically, as shown in FIG. 3c, the "U"-shaped loop 129 of the cradle 116 is closest to the surgical tool 120. This ensures that a vein 118 or other tissue of interest is retracted away from the surgical tool 120 to facilitate manipulating the surgical tool 120 relative to the side branch or other tissue.

Figure 4A:
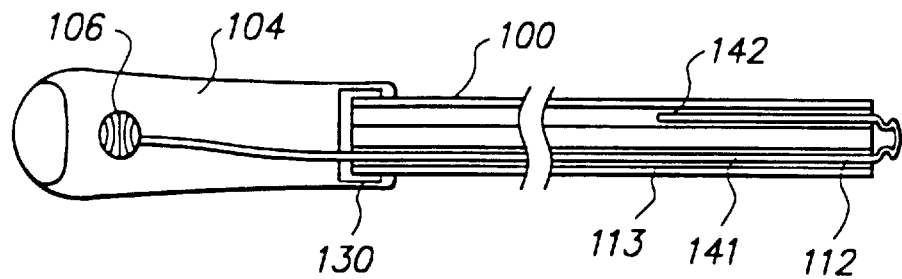
FIG. 4a is a cut-away top view of cannula 100.
Figure 4B:
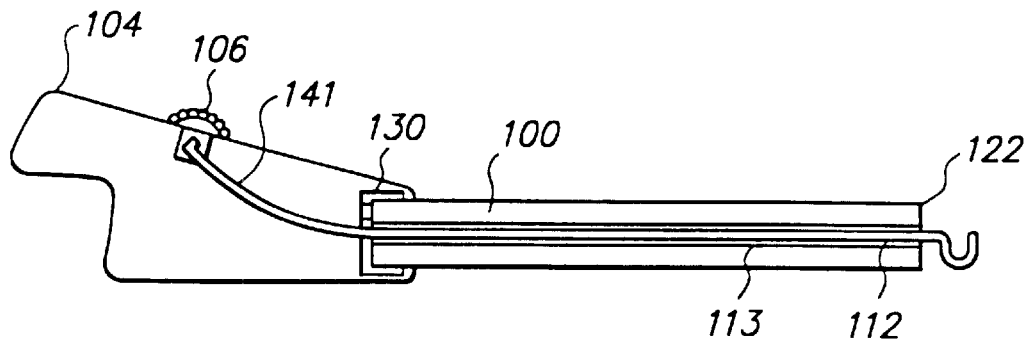
FIG. 4b is a cut-away side view of cannula 100.

FIG. 4a is a cut-away top view of cannula 100. The retractor 112 is slidably positioned within minor lumens 113 along the length of the cannula 100 within close tolerances in order to position the retractor 112 stably within the cannula 100. For example, in one embodiment retractor legs 141, 142 are approximately 0.045 inches in diameter and the lumens 113 encasing the legs 141, 142 are approximately 0.080 inches in diameter, as friction between the legs of the retractor 112 and the lumens 113 holds the retractor stably within the cannula. This configuration restricts rotational movement of the retractor to provide more stable retraction as compared with conventional retractors. The legs 141, 142 of the retractor 112 are formed of flexible, resilient material and are retained within the lumen 113 in substantially straight or flat orientation, but may return to a material bend or curve, as illustrated in FIG. 5a, as the retractor 112 is extended from the distal end of the cannula 100.

The leg 141 of the retractor 112 passes through a sliding gas or fluid seal 130 at the proximal end of the lumen 113. The leg 141 of the retractor 112 passes out of the cannula 100 and into handle 104 for attachment to a slider button 106 for facilitating translational movement of the retractor 112 from the proximal or handle end of the cannula 100. However, other types of control devices such as knobs, grips, finger pads, and the like may be linked in conventional ways to the retractor 112 in order to manually control the translational movement of retractor 112. In one configuration, the proximal end of leg 141 is bent relative to the axis of the cannula, and the button 106 is attached to the bent position of the leg 141 to facilitate moving the button 106 and the retractor 112 traditionally under manual control. The button 106 preferably includes lateral grooves to prevent finger or thumb slippage during sliding manipulation of the retractor 112.

Thus, in the operation of a preferred embodiment, a user actuates the slider button 106 to extend retractor 112 out of the lumen 113 at the distal end of the cannula 100. In one embodiment, the resilient retractor 112 is formed in a smooth bend, as shown in FIG. 2a, and gradually deflects away from the central axis 101 of the cannula 100 as the retractor is extended. Upon encountering the target vessel or tissue of interest, the vessel is restrained in the cradle 116, and a lateral resilient force is exerted on the target vessel in a direction away from the cannula The vessel is thus pushed away from the axis of the cannula 100, isolating it from surrounding tissue or adjacent vessels such as tributaries or side branches. As a tributary is thus isolated, a surgical tool 120 such as cauterizing scissors may be safely employed to operate on the tributary without harming the saphenous vein 118. When retracted into the cannula 100, the retractor 112 is again resiliently straightened or flattened.

Figure 5A:
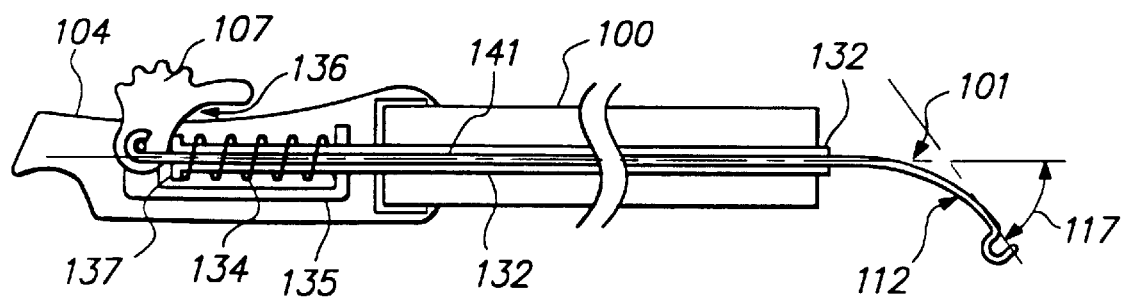
FIG. 5a is a cut-away view of a sliding tube embodiment of cannula 100 in a first position.
Figure 5B:
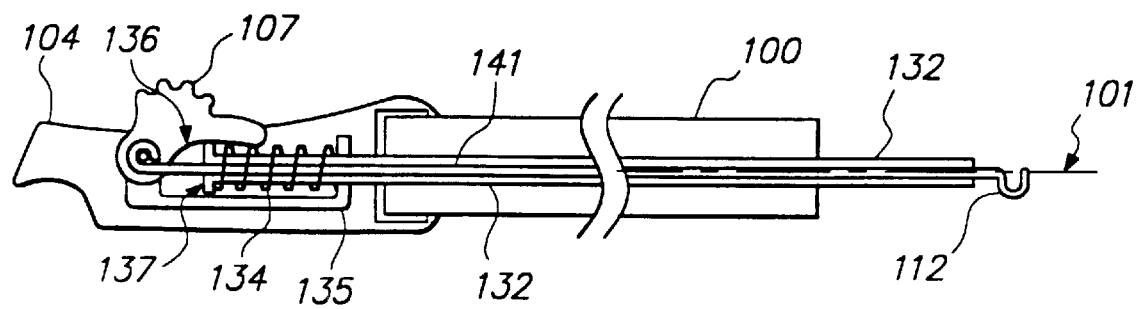
FIG. 5b is a cut-away view of the sliding tube embodiment of FIG. 5a in a second position.

In an alternate embodiment as illustrated in FIGS. 5a and 5b, a sliding tube 132 is added to provide operational versatility to cannula 100. In a first position, the sliding tube 132 is retracted and the retractor 112 protrudes from the distal end at an angle with respect to the central axis 101 of the cannula 100. In a second position, the sliding tube 132 is extended out, temporarily straightening the retractor 112. As illustrated in FIG. 5a, a sliding tube 132, in a first position encases the retractor 112 up to the point at which the retractor 112 curves away from the central axis 101 of the cannula thus allowing the retractor 112 to displace and isolate a target vessel. The proximal end of the sliding tube 132 is linked to button 107 for translationally moving retractor 112 as well as actuating the sliding tube 132. In one embodiment, as illustrated in FIG. 5a, the sliding tube 132 is in a first position with the button 107 in an upright position. A spring 134 is coupled between a support structure 135 and the proximal end 137 of the sliding tube 132. In the first position of sliding tube 132, the spring 134 is extended fully and exerts little or no force on the sliding tube 132. Of course, sliding tube 132 may be manually manipulated without linkage to a button 107.

To extend the sliding tube 100, button 107 is pushed down. As illustrated in FIG. 5b, the button 107 has a cam surface 136 which pushes on the proximal end 137 of the sliding tube 132 as the button 107 is pressed. The sliding tube 132 is pushed forward, overcoming the resilient force of sprint 134, to encase the retractor 112 and decrease angle 117 between the distal end of the retractor 112 and the central axis 101 of the cannula 100. Upon releasing the button 107, the spring force urges the proximal end 137 of the sliding tube 132 back toward the first position against button 107. The sliding tube 132 is formed of material having sufficient strength to force the retractor 112 to straighten out the angle 117, and the retractor 112 is formed of resilient material having a sufficient flexibility to straighten out the angle 117 in response to a tube 132 being slid over the retractor 112, but having sufficient rigidity to cradle and dissect a target vessel. Resiliency of the retractor 112 ensures return to the downwardly-curved shape after being released from tube 132. Thus, in accordance with this embodiment, a user may employ the curved retractor for certain applications and employ the straightened form for other applications. A manual actuator may be configured in other ways than button 107 to extend the sliding tube 132 in response, for example, to being pulled up instead of pushed down.

Figure 6A:
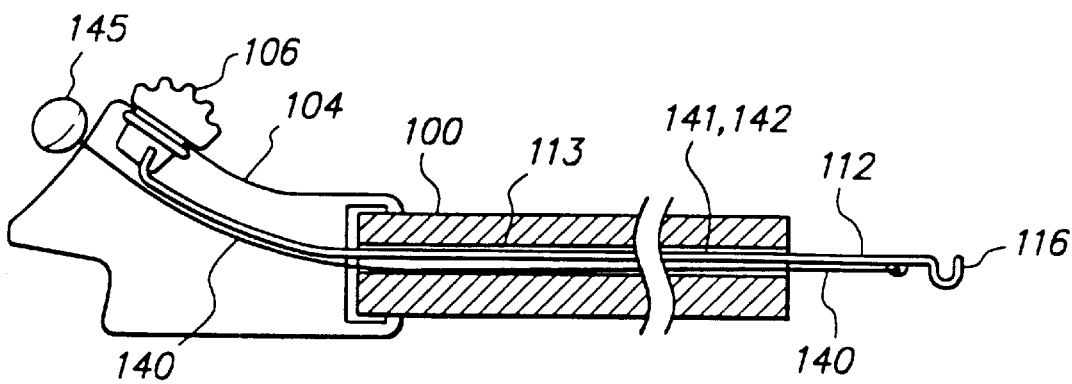
FIG. 6a is a cut-away view of an embodiment of cannula 100 having an angling device 140.
Figure 6B:
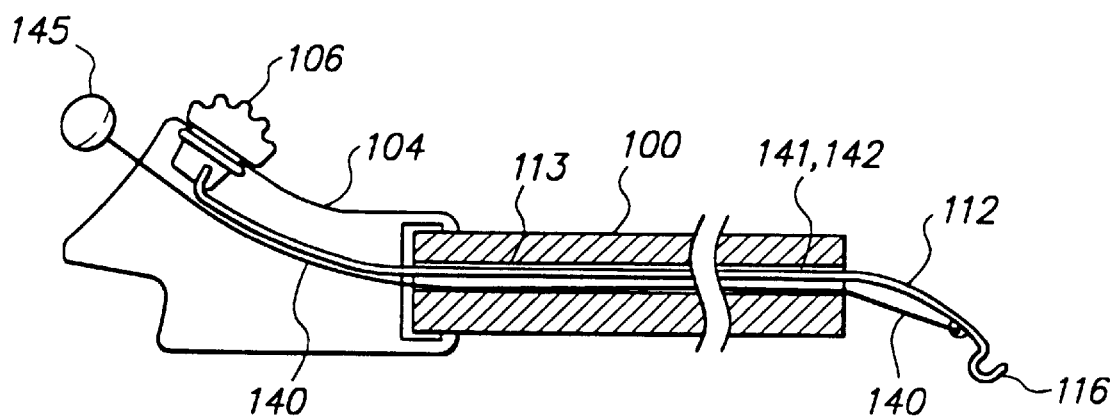
FIG. 6b is a cut-away side view of the apparatus illustrated in FIG. 6a in which the retractor 112 is extended and the angling device 140 is actuated.

Another embodiment employs a retractor 112 which has a naturally straight shape. As illustrated in FIGS. 6a and 6b, an angling device 140 is disposed between the distal end of the retractor 112 and the proximal end of the cannula. The angling device 140 may be positioned within the same lumens 113 as the retractor 112 and preferably may comprise two wires coupled to points below the cradle 116 of the retractor 112 substantially in parallel positions on each of the legs 141, 142.

Figure 6C:
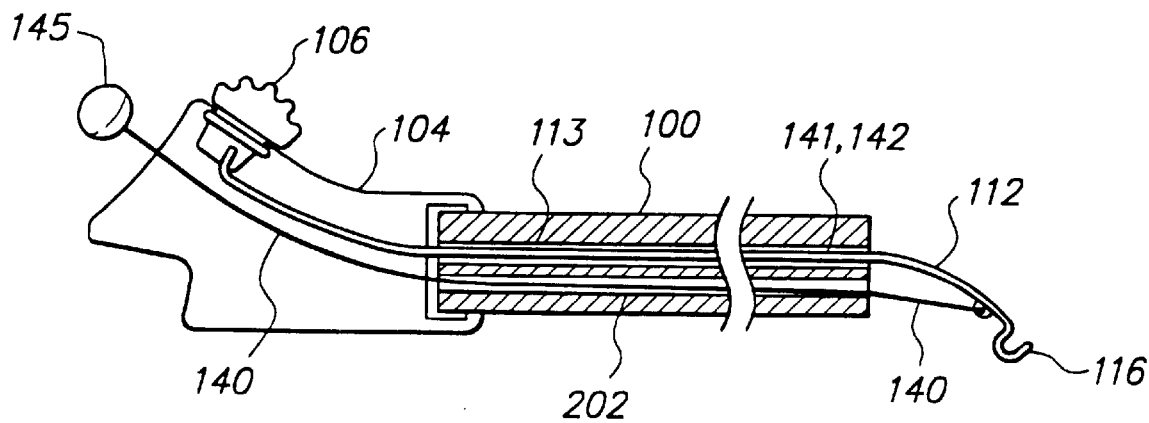
FIG. 6c is a cut-away side view of the angling device embodiment in which the angling device 140 is in a separate lumen from the retractor 112.

Upon extending the retractor 112 using button 106, the angling device 140 is extended with the retractor 112. The angling device 140 is coupled to a handle 145 at the proximal end of the cannula 100 to facilitate establishing an angle in the retractor 112 by pulling with a backward force on the angling device 140. As illustrated in FIG. 6b, after the retractor 112 is extended. the angling device 140 is actuated and a bend is created in the retractor 112 as the backward force exerted on the distal end of the retractor is exerted against the relatively fixed position of the retractor legs 141, 142 disposed within the lumens 113. As shown in FIG. 6c, the angling device 140 may also be located in a separate lumen 202 from the retractor 112 with part of the angling device 140 positioned outside of the cannula 100 when the retractor 112 is in the retracted position.

Figure 7A:
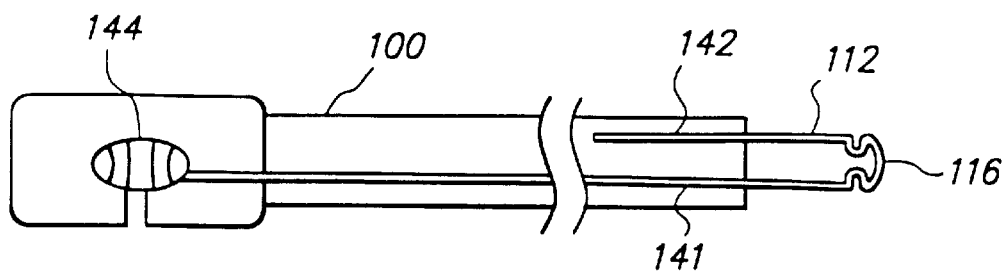
FIG. 7a is a cut-away side view of a twistable retractor 112 in a straight position.
Figure 7C:
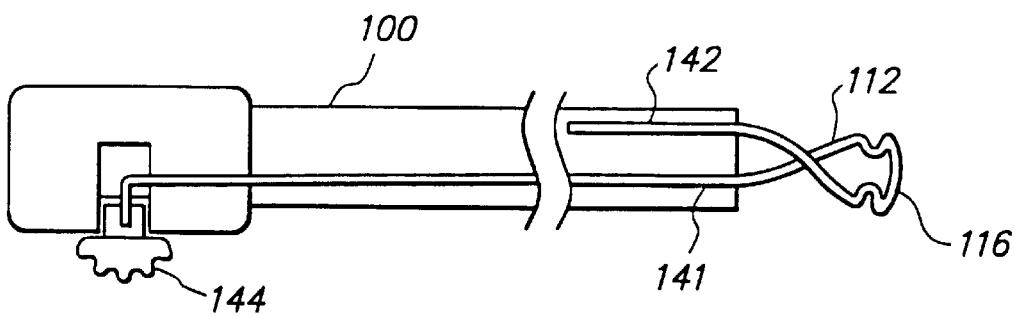
FIG. 7c is a cut-away side view or twistable retractor 112 in a crossed position.
Figure 7B:
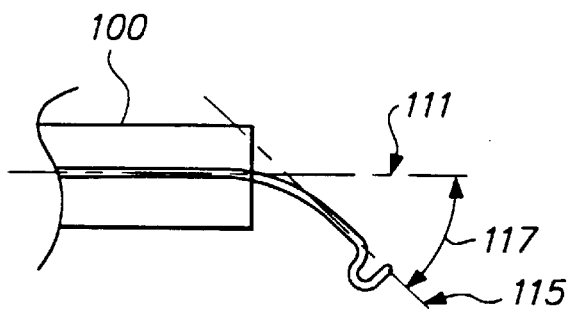
Figure 7D:
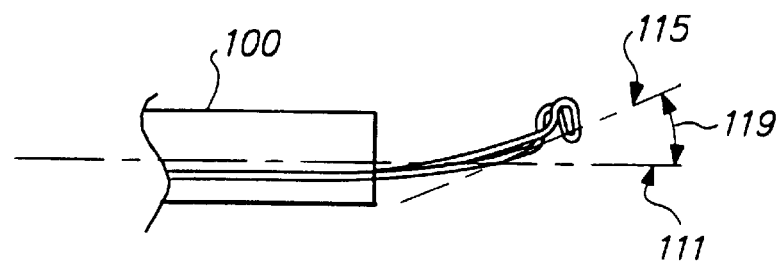
FIG. 7d is a side view of the retractor 112 of FIG. 7c.

FIG. 7a illustrates another embodiment of cannula 100 in which the retractor 112 is pre-formed with one leg 141 of the retractor 112 bent at an angle at its proximal end skewed to the axis of the distal end of the other leg 142. The bent portion of the leg 141 may be linked to a sliding knob 147 for convenient manual manipulation of this embodiment of the invention. Upon sliding the knob 147, the leg 142 coupled to knob 147 is twisted rotationally. The two legs 141, 142 of retractor 112 are coupled together via cradle 116. The axis of the second portion of the retractor 112 in the first position is at a first angle 117 to the axis of the cannula 100, as shown in FIG. 7b. As knob 147 is moved, leg 141 is rotated and crosses under leg 142, as shown in FIG. 7c. This causes cradle 116 to flip 180 degrees and bends the retractor 112 at a second angle 119, as shown in FIG. 7d. Thus, if a vessel is disposed on one side of cradle 116 or cannula 100 while the retractor 112 is in the first position, then upon rotating the knob 147, the vessel is transported to the other side of the cannula 100. This allows the user to isolate the vessel by simply actuating knob 147.

Figure 8A:
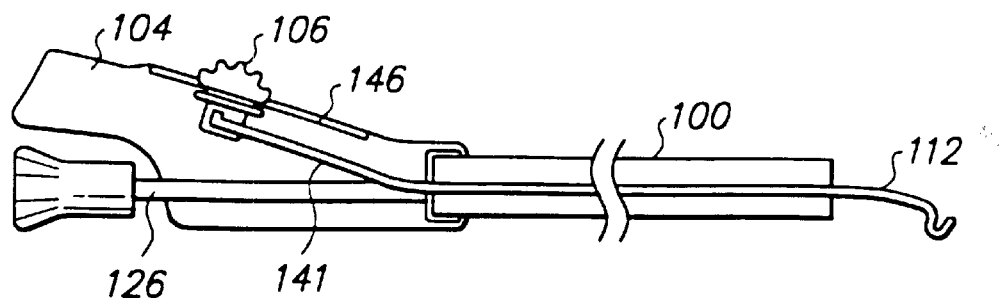
FIG. 8a is a cut-away side view of the handle 104.
Figure 8B:
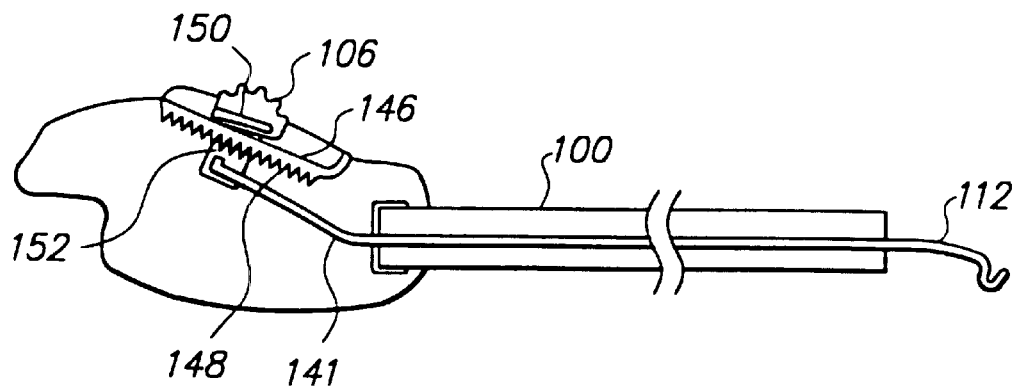
FIG. 8b is a cut-away side view of an alternate embodiment of handle 104.

FIG. 8a illustrates a cut-away side view of button 106 on the handle 104 of cannula 100, with an endoscope 126 positioned within cannula 100. As mentioned above, button 106 is coupled to one leg 141 of the proximal end of retractor 112. Sliding the button 106 in groove 146 translationally moves the retractor 112. Groove 146 is preferably minimally wider than the shaft of button 106 to minimize excessive horizontal movement of button 106 while still allowing smooth translational movement of button 106. As illustrated in FIG. 8b, the button 106 may include locking or ratcheting teeth 152 to give tactile feedback of its location, and to positively retain the button and the associated leg 141 in an extended or retracted position. Several mating teeth 148 are located underneath groove 146, and a spring member 150 is attached to button 106 to exert pressure against the base of groove 146, to engage mating teeth 148, 152. When a force is applied on the top of button 106, the interlocking sets of teeth are disengaged and button 106 can move freely. Upon achieving the desired extension or retraction the leg 141, button 106 is released and is retained place by the engaged teeth 148, 152.

Figure 9A:
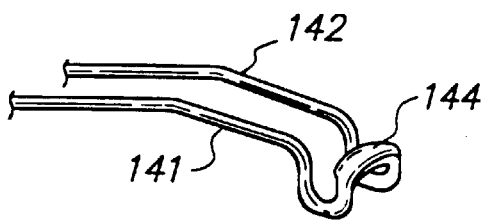
FIG. 9a is a side view of cradle 116.

FIG. 9a illustrates a top view of cradle 116 in an embodiment in which the cradle 116 is formed by two legs 141, 142 of retractor 112. The distal end of the legs form "U"-shaped side guides. The top 144 of the distal portion of the "U" is preferably flattened. This provides atraumatic support or the target vessel retained within cradle 116. Additionally, by minimizing the thickness of distal portion 144, contact with other devices in close proximity with retractor 112 is minimized.

Figure 9B:
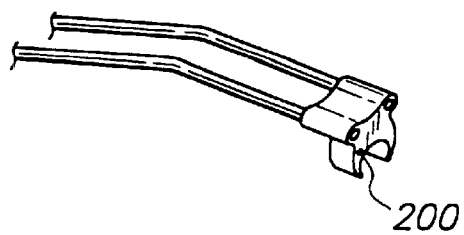
FIG. 9b illustrates a first alternate embodiment of cradle 116.

The cradle 116 may have other effective shapes, for example, as illustrated in FIG. 9b in which a "C" ring element is attached to legs of the cradle 116. The "C" ring may have a small hole 200 in one side with an axis approximately parallel to the axis of the retractor 112. This hole 200 is used to hold suture or other ligating materials, and may also be used as a knot pusher. As shown in FIGS. 10a and 10b, in an alternate embodiment of the embodiment of FIG. 9b, the retractor 112 is formed and flattened and a "C"-shaped ring is coupled to the retractor 112 by, for example, gluing or molding the "C" ring to the distal end of the retractor 112, as shown in FIGS. 10c and 10d.

Figure 9C:
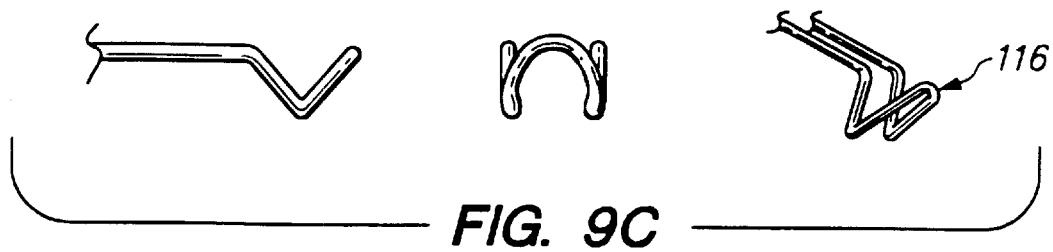
FIG. 9c illustrates multiple views of a second alternate embodiment of cradle 116.
Figure 9D:
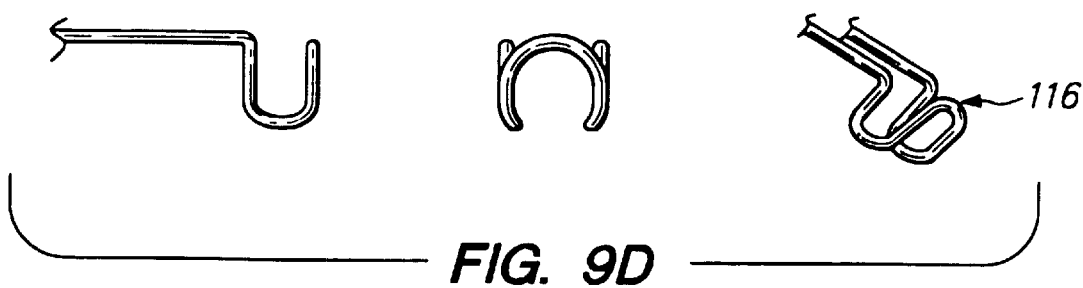
FIG. 9d illustrates multiple views of a third alternate embodiment of cradle 116.
Figure 9E:
FIG. 9e illustrates multiple views of a fourth alternate embodiment of cradle 116.

Referring back to FIGS. 9c, 9d, and 9e, the side guides of the cradle may include a loop 129 in a "V" shape, an arced "U" shape, or a semi-circular shape. In one embodiment, as illustrated in FIG. 9f, the retractor 112 has only one leg 141, and the cradle 116 is formed by the leg 141. A stopper 160 is coupled to the end of the leg 141 to serve as a guide to retain the target vessel, and add a blunt surface to the end of the wire, for example, for pushing and probing tissue. FIG. 9g illustrates a retractor 112 having a spur 204 formed in one or both legs 141, 142 for allowing the retractor 112 to be used for dissection. Sinusoidal, half-sinusoidal, and other geometric configurations may be used equally effectively as the shape of loop 129 in accordance with the present invention.

Figure 11:
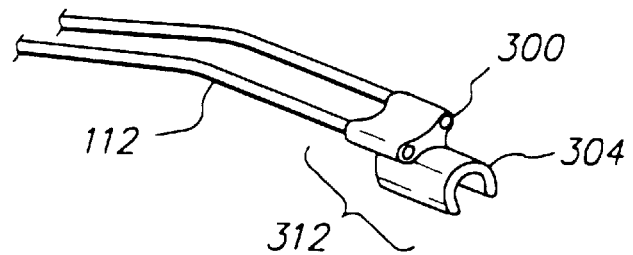
FIG. 11 illustrates a perspective side view of cradle 312 for remotely ligating vessel.

FIG. 11 illustrates an alternate dissection cradle 312 for use in remote vessel ligation. Remote vessel ligation as discussed above is necessary to provide hemostasis to a vessel or other tissue after the vessel has been transected. In accordance with the present invention, hemostasis is accomplished by tightening suture formed in a loop adjacent the point of transection of the vessel. However, it is preferable to provide hemostasis to the vessel without incising the body a second time at the point of transection. The cannula 100 and dissection cradle 312 provide this functionality.

Figure 12:
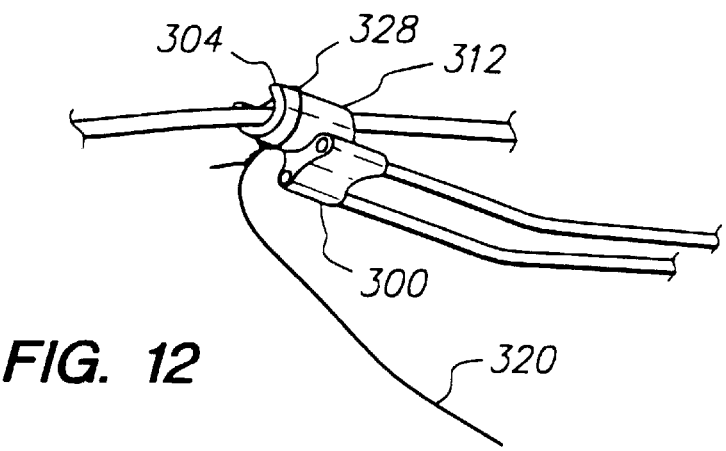
FIG. 12 illustrates a perspective side view of cradle 312 in operation.

At the distal end of the retractor 312, a shoulder part 300 is preferably formed of a rigid plastic encapsulating the distal end of the retractor 112. A curved channel part 304 is attached to the shoulder 300. The cured channel 304 is formed in the shape of a "C" as shown. The curve of curved channel 304 exposes a portion of the distal face of the shoulder 300, upon which a suture loop 328 may be abutted, as shown in FIG. 12. Other shapes, such as those shown in FIGS. 9a–e, may also be used as curved channel 304.

FIG. 12 illustrates the manner in which the suture loop 328 is transported safely to the point of transection. The loop 328 is formed as a slipknot, which may be cinched tighter by exerting a backwards force on the free end of the suture 320. The suture loop 328 is tied around the vessel and the curved channel part 312, and is abutted against the shoulder 300. Next, the loop 328 is tightened onto the curved channel 304 by pulling back on the free or proximal end of the suture 320. The loot 328 is tightened sufficiently to permit safe advancement, but is provided with sufficient slack to allow displacement of the loop 328 onto the vessel adjacent the point of transection upon retraction of the retractor 312 into the cannula 100.

Figure 13:
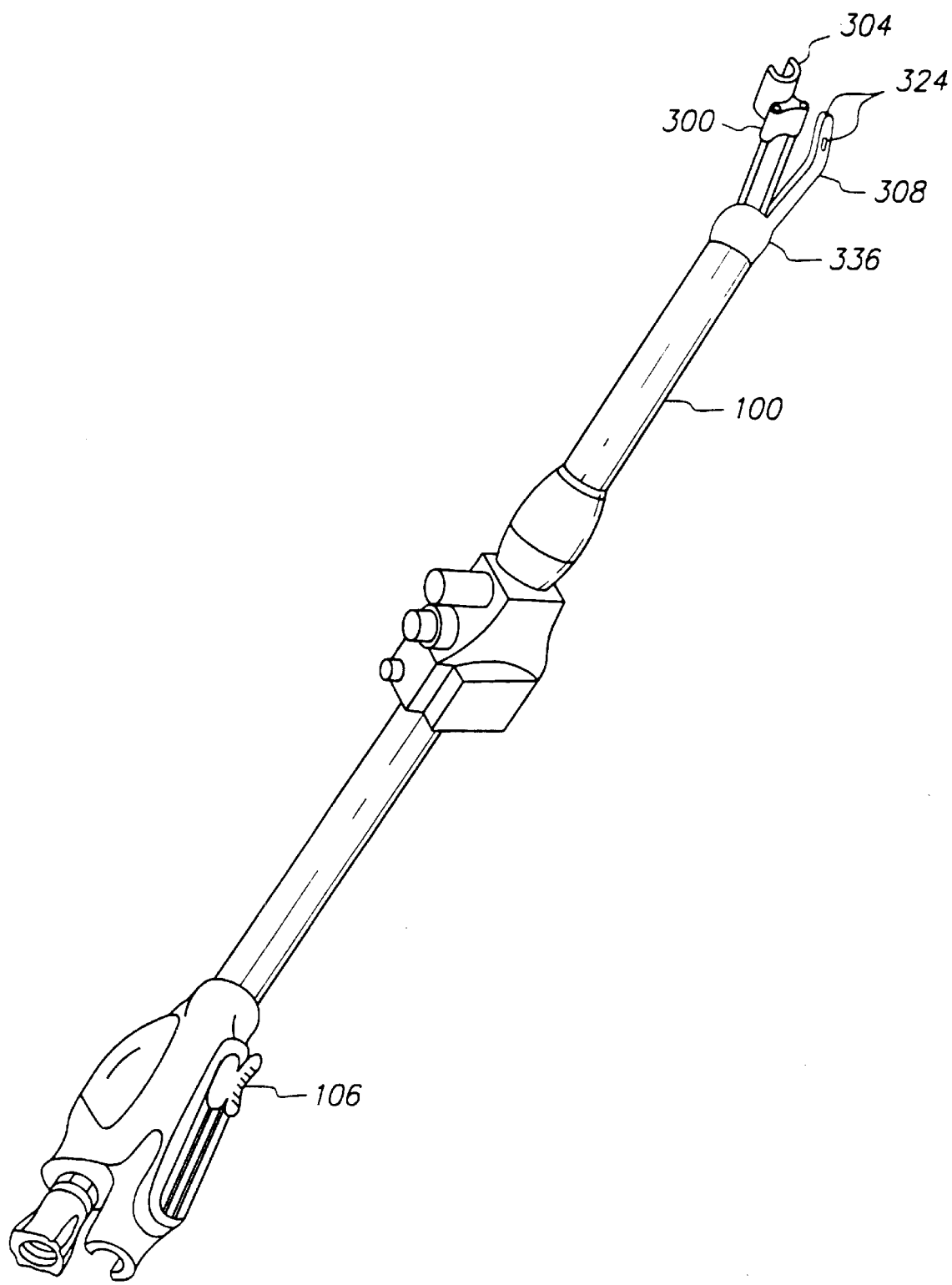
FIG. 13 illustrates a perspective side view of cannula 100 having a dissection cradle 312.

One embodiment of the present invention for exerting a backward or disengaging force on the loop 328 is shown in FIG. 13. FIG. 13 illustrates a tension mount 308 attached to cannula 100 for providing secure transport of the suture 320 to the surgical site of interest and for providing a controlling mechanism for tightening the suture loop 328 around the vessel when ligation is desired. The tension mount 308 is also formed of rigid plastic with some flexibility to allow other surgical tools 120 (not shown) to extend beyond the distal end of the tension mount 308, and to allow atraumatic advancement of the tension mount 308 through the body. The distal end of the tension mount 308 includes a hole 324 through which the suture is threaded to tighten the suture loop 328. The distal end of the tension mount 308 protrudes toward the central axis of the cannula 100. This ensures that the vessel and the suture will be in the optimal position for transection or cutting after the loop 328 has been displaced onto the vessel. Additionally, the forward angle of the tension mount 308 also ensures that the loop 328 will be displaced onto the vessel upon retraction of the retractor 312, as discussed in greater detail below. The length of the tension mount 308 is chosen to allow the cradled vein to remain in endoscopic view upon advancement.

Alternatively, a long knot pusher may be used in place of tension mount 308. The suture 320 is looped around the vessel and the curved channel 304, previously described. However, the free end of the suture 320 is threaded through a hole in the long knot pusher disposed within the cannula 100. The cannula 100 and knot pusher are advanced to the point of transection. Displacement of the loop 328 occurs by advancing the knot pusher while maintaining the position of the dissection cradle 312 relative to the vessel. After the loop 328 is displaced onto the vessel, the loop 328 is tightened by pulling backward on the suture 320. The long knot pusher may contain a lumen which runs the length of the cannula 100 or it may contain a shorter lumen which starts at the tip of the cannula and exits a side of the cannula 100 after a short distance proximally.

FIG. 14a illustrates the operation of the cannula 100 which has a tension mount 308. The cradle 312 holds a vessel 330. The vessel 330 is safely cradled in the curved channel 304 as the cannula 100 is advanced. The suture 320 is threaded through the hole 324 disposed in the distal end of the tension mount 308. The distal end of the suture 320 is then formed into a suture loop 328 around the vessel 330, and is abutted against the shoulder 300. In this embodiment, the proximal end of the suture 320 is wrapped around a cleat 332 on button 106 at the proximal end of the cannula 100. The loop 328 is tightened around curved channel 304 by winding the proximal end of the suture 320 around the cleat 332 which has the effect of pulling on the suture loop 328 and cinching, the knot tightly around the curved channel 304 against the shoulder 300. The suture loop 328 may now be safely advanced to the surgical site as excessive slack does not occur in the loop 328, which would cause the loop 328 to be dislodged from the cradle 302. In an alternate embodiment, the loop 328 is tightened responsive to the sliding of the button 106. The button 106 has a lock with a release mechanism which restricts the sliding of the button 106. When the loop 328 requires tightening after displacement onto the vessel, the lock is released and the button 106 is retracted. This embodiment ensures that the surgeon does not accidentally dislodge the loop 328 from the shoulder 300 by prematurely retracting the retractor 312 into the cannula 100.

Upon reaching the site of interest, the loop 328 is displaced onto the vessel 330 by sliding a manual controller backwards, causing the retractor 112 to retreat to an axial position. In the embodiment of FIGS. 14a and b, the loop 328 is displaced by sliding the button 106 backwards. Upon sliding the button 106 backwards, as shown in FIG. 14b the cradle 312 is retracted into cannula 100, causing the loop 328 to be forcibly displaced from the shoulder 300 of the dissection cradle 312 onto the vein 330 at the desired location.

After displacement onto the vessel 330, a knot tightener 340 is then used to tighten the suture loop 328 onto the vessel 330 to provide hemostasis. In the embodiment of FIGS. 14a and b, the loop 328 is tightened onto the vessel 330 as the proximal end of the suture 320 is wound around the cleat 332. The proximal end of the suture 320 could also simply be detached from the proximal end of the cannula 100, and the loop 328 tightened by pulling on the free end of the suture 320. Alternatively, the loop 328 may be tightened by fixing the proximal end to the button 106. Sliding the button 106 towards the proximal end of the cannula 100 exerts a backwards force on the loop 328, tightening the loop 328.

Figure 15:
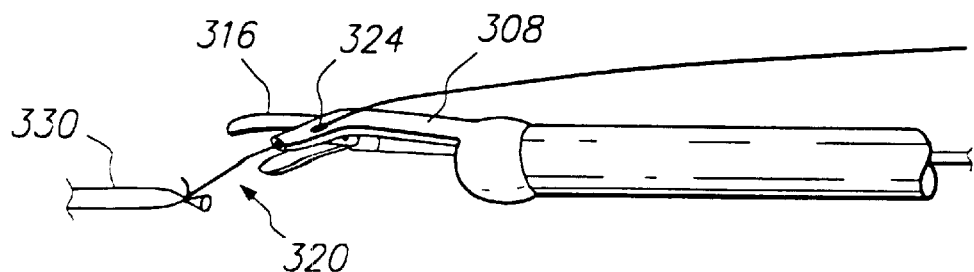
FIG. 15 illustrates a perspective side view of cannula 100 with transection device 316.

FIG. 15 illustrates the use of the transection instrument 316 in accordance with the present invention. The transection instrument 316 is preferably endoscopic shears disposed within cannula 100. The shears 316 are positioned between tension mount 308 and cradle 312. After the vessel 330 has been ligated as described above, the shears 316 are extended to transect the vessel. As the vessel is tied by the suture 320 which passes into the tension mount 308, the vessel is thus placed within easy reach of the blades of the shears 316. The tension mount 308 is formed with a slight bend toward the center of the cannula 100 to facilitate keeping the vessel 330 within the apex of the open blades of the shears 316. After transecting the vessel 330, the vessel 330 will fall away as shown in FIG. 15. The suture 320, however, is now within the apex of the open blades of the shears 316. The shears 316 are then extended again and used to cut the suture 320. The ligated vessel 330 remains in the surgical site, and the graft is able to be removed through the first and only incision.

Figure 16A:
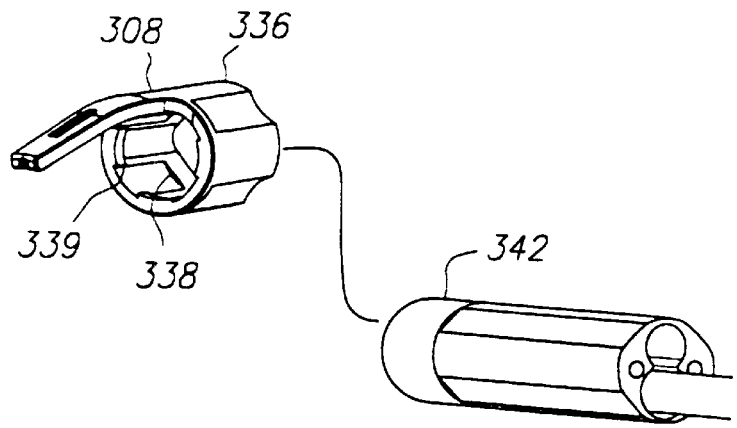
FIGS. 16a–c illustrates multiple views of tension mount 308.
Figure 16B:
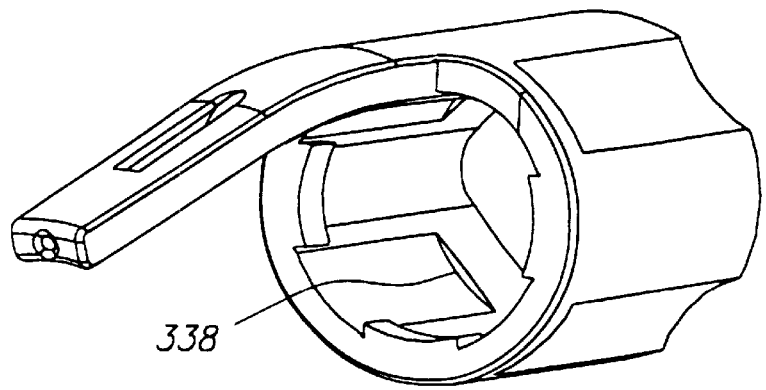
Figure 16C:
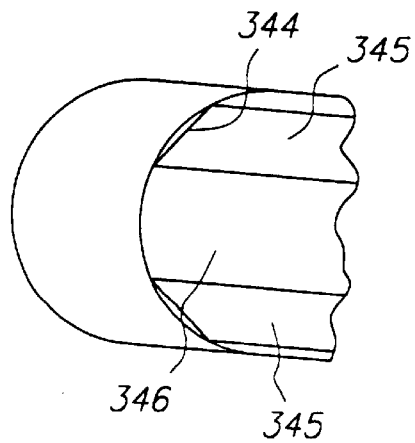

FIGS. 16a–c illustrates multiple views of tension mount 308. FIG. 16a illustrates tension mount 308 attached to a collar 336. The collar 336 allows the cannula 100 to be used without a tension mount 308 for the initial transection operation in which the tributaries of the vessel 330 are transected to allow the main length of the vessel to be extracted from the body. For this initial transection operation, the tension mount 308 may interfere with this procedure, and thus should be removed.

The collar 336 of the tension mount 308 has proximal and distal ridges 338, 339 disposed on its inner surface. FIG. 16b illustrates in greater detail the proximal ridge 338 which mates with ridges disposed on the cannula surface. As shown in FIG. 16c, the distal end 342 of the cannula 100 is smooth plastic or other bioinert material on which the ridged collar 336 may slide easily. Ridges 346 situated at flat or recessed portions 345 on the surface of the body of cannula 100 form edges 344 for retaining the collar 336. Upon sliding the collar 336 onto the distal end 342 of the cannula 100, the collar 336 resiliently expands and ridges 338, 339 of the collar 336 align with edges 344 of the cannula 100. Upon alignment, the collar 336 resiliently contracts and thus forms a secure fitting of collar 336 on cannula 100. When the surgeon wants to remove the collar 336, the surgeon simply twists the collar 336 to misalign the ridges 338, 339 of the collar with ridges 346 of the cannula 100, causing the collar 336 to resiliently expand again, thus allowing the collar 336 to be easily removed from the cannula 100.

Figures 17, 18:
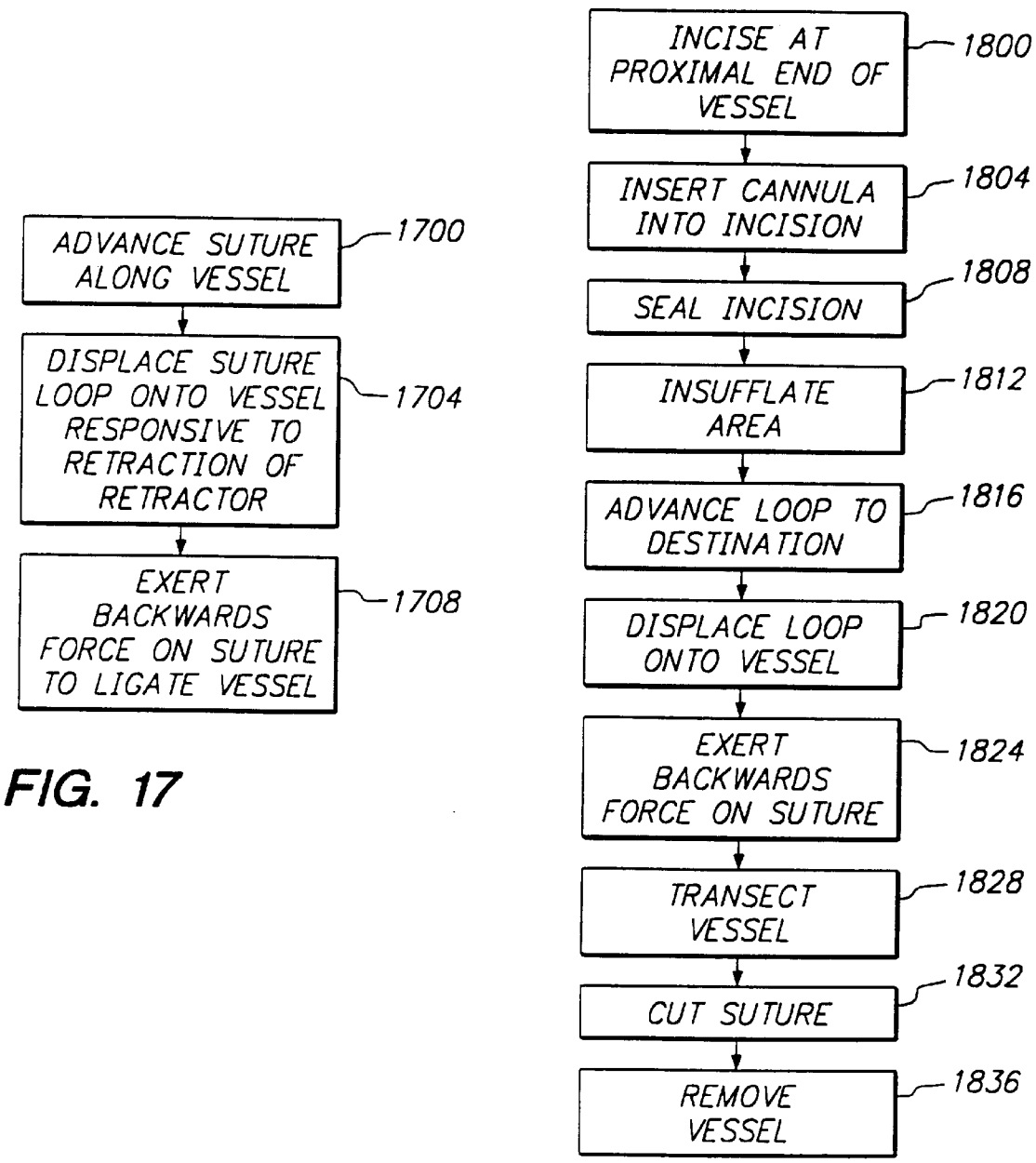
FIG. 17 is a flowchart illustrating the process of remote ligation of a vessel in accordance with the present invention.
FIG. 18 is a flowchart illustrating the process of remote ligation and vessel harvestation under gas insufflation.

FIG. 17 illustrates a method of performing remote vessel ligation in accordance with the present invention. The surgeon advances 1700 a suture loop 328 along a vessel to a remote site from incision. The suture loop 328 is displaced 1704 onto the vessel responsive to retraction of the retractor, and, responsive to exerting 1708 a backward force on the suture, the vessel is ligated.

In a further embodiment, as shown in FIG. 18, the one-incision ligation and harvesting operation is performed under gas insufflation. First, an incision is made 1800 at the desired beginning point of the graft. For example, for saphenous vein harvesting for coronary artery bypass grafting, the incision is made at the knee. Next, the cannula 100 is inserted 1804 into the incision, and the incision is sealed 1808. A tunnel is formed along the vessel by insufflating 1812 the area with gas. The suture loop 328 is safely advanced 1816 to the destination. For saphenous vein harvesting, the loop 328 is advanced to its origin at the saphenofemeral junction. The loop 328 is displaced 1820 onto the vessel, and a backwards force is applied 1824 to the suture 320 to ligate the vessel. The vessel is transected 1828 and the suture is cut 1832. The vessel can now be removed 1836 from the original incision.

Thus, in accordance with the present invention, only one incision is required to harvest and ligate vessel in accordance with the present invention. The use of dissection cradle 312 allows the suture loop 328 of suture 320 to be advanced safely to the surgical site without being caught on the main trunk of the vessel or side branches thereof. The tension mount 308 accurately and reliably positions the vessel for transection and the suture 320 for cutting and provides the tension required to tighten the suture loop 328 of suture 320 onto a forward shoulder of the curved channel 304 for safe advancement and tensioning as required to provide hemostasic transection and harvesting of a target vessel.

What is claimed is:

1. A method of surgery with an elongated cannula for harvesting and remotely ligating vessels including a retractor having a dissection cradle for contacting vessels and supporting a suture loop thereon, the method comprising:

incising an entry point near a proximal end of the vessel to be harvested;

inserting the cannula into the incision;

sealing the incision;

insufflating a tunnel along the vessel;

supporting the suture loop in an open configuration;

advancing the suture loop to a remote site from the incision;

displacing the suture loop onto the vessel;

exerting a backward force on the suture to ligate the vessel.

2. A surgical apparatus for remotely ligating a vessel using a suture loop comprising:

an elongated cannula having a central axis between distal and proximal ends;

a retractor, having a first portion disposed near the proximal end of the cannula and a second portion disposed near the distal end of the cannula, the second portion having a dissection cradle positioned at the distal end of the second portion, the dissection cradle comprising:

a shoulder part, on a distal end of the retractor;

a curved channel part, attached to a distal end of the shoulder part to allow the suture loop to abut against the distal end of the shoulder upon translation of the cannula.

3. The apparatus of claim 2 further comprising:

a knot pusher, slidably disposed within the cannula, having a distal end attached to a distal end of the suture to allow the loop to be displaced onto the vessel responsive to translation of the knot pusher.

* * * * *

UNITED STATES PATENT AND TRADEMARK OFFICE
CERTIFICATE OF CORRECTION

PATENT NO. : 6,348,037 B1
DATED : February 19, 2002
INVENTOR(S) : Albert K. Chin et al.

It is certified that error appears in the above-identified patent and that said Letters Patent is hereby corrected as shown below:

<u>Title page,</u>
Item [73], delete "Edwin J. Heavka" and replace with -- Edwin J. Hlavka --

Signed and Sealed this

Fourth Day of June, 2002

Attest:

JAMES E. ROGAN
Attesting Officer *Director of the United States Patent and Trademark Office*